United States Patent
Tyagi et al.

(10) Patent No.: US 7,230,097 B2
(45) Date of Patent: Jun. 12, 2007

(54) PROCESS FOR PREPARATION OF 7-[α-AMINO (4-HYDROXYPHENYL) ACETAMIDO]-3-SUBSTITUTED-3-CEPHEM-4-CARBOXYLIC ACID

(75) Inventors: Om Dutt Tyagi, Pune (IN); Dnyandev Ragho Rane, Pune (IN); Tushar Kumar Srivastava, Pune (IN); Krishnarao Tukaram Sirsath, Pune (IN)

(73) Assignee: Lupin Ltd., Mumbai (IN)

( * ) Notice: Subject to any disclaimer, the term of this patent is extended or adjusted under 35 U.S.C. 154(b) by 264 days.

(21) Appl. No.: 10/801,443

(22) Filed: Mar. 15, 2004

(65) Prior Publication Data
US 2005/0113570 A1 May 26, 2005

(30) Foreign Application Priority Data
Mar. 10, 2003 (IN) ...................... 1031/MUM/2003

(51) Int. Cl.
*C07D 501/22* (2006.01)
*C07D 501/04* (2006.01)
(52) U.S. Cl. ........................................ 540/215; 560/39
(58) Field of Classification Search ................ 540/215
See application file for complete search history.

(56) References Cited

U.S. PATENT DOCUMENTS

| | | | |
|---|---|---|---|
| 3,249,622 A | 5/1966 | Herrling et al. | |
| 3,499,909 A | 3/1970 | Weissenburger et al. | |
| 3,575,970 A | 4/1971 | Weissenburger et al. | |
| 3,595,855 A | 7/1971 | Robinson et al. | |
| 3,654,266 A | 4/1972 | Robinson et al. | |
| 3,970,651 A | 7/1976 | Kaplan et al. | |
| 3,985,741 A | 10/1976 | Crast, Jr. et al. | |
| 3,985,747 A | 10/1976 | Kaplan et al. | |
| 4,218,474 A | 8/1980 | Barnish et al. | |
| 4,520,022 A | 5/1985 | Hoshi et al. | |
| 4,694,079 A | 9/1987 | Crast, Jr. | |
| 4,699,979 A | 10/1987 | Hoshi et al. | |
| 6,903,211 B2 * | 6/2005 | Deshpande et al. | 540/215 |

FOREIGN PATENT DOCUMENTS

| | | |
|---|---|---|
| GB | 959853 | 3/1964 |
| GB | 1008468 | 10/1965 |
| GB | 1 339 605 | 12/1973 |
| GB | 1 532 682 | 11/1978 |
| WO | 98/04732 | 2/1998 |
| WO | 03/011871 | 2/2003 |

* cited by examiner

*Primary Examiner*—Mark L. Berch
(74) *Attorney, Agent, or Firm*—Merchant & Gould P.C.

(57) ABSTRACT

A process for preparation of 7-[D-α-amino-α-(4-hydroxyphenyl)acetamido]-3-(1-propen-1-yl)-3-cephem-4-carboxylic acid viz. Cefprozil of formula (I) in high purity, substantially free of impurities,

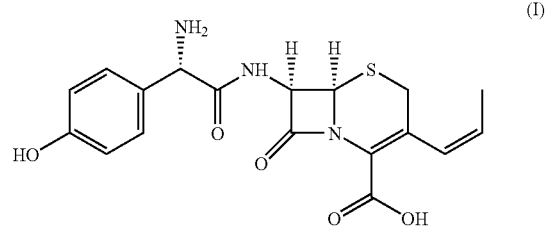

(I)

which comprises preparation of mixed acid anhydride by selecting the sequence and temperature of addition of the reagents and its subsequent condensation with a protected 7-APCA; followed by hydrolysis, isolation and purification to give Cefprozil of formula (I) in the form of a monohydrate.

33 Claims, No Drawings

PROCESS FOR PREPARATION OF 7-[α-AMINO (4-HYDROXYPHENYL) ACETAMIDO]-3-SUBSTITUTED-3-CEPHEM-4-CARBOXYLIC ACID

FIELD OF THE INVENTION

The present invention provides a novel process for preparation of 7-[D-α-amino-α-(4-hydroxyphenyl)acetamido]-3-(1-propen-1-yl)-3-cephem-4-carboxylic acid viz. Cefprozil of formula (I) in high purity, substantially free of impurities.

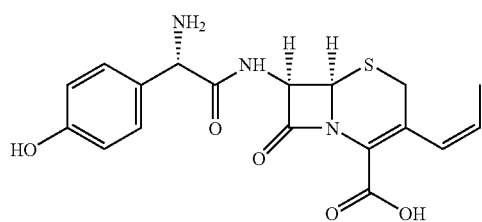

(I)

BACKGROUND OF THE INVENTION

Cefprozil, as disclosed in U.S. Pat. No. 4,520,022, is a commercially valuable and therapeutically useful semi-synthetic, broad-spectrum oral cephalosporin antibiotic effective in controlling diseases caused by a wide variety of Gram positive and Gram negative microorganisms.

Because of its therapeutic usefulness and broad, efficient spectrum of activity, there is always a need for an improved synthetic process which would result in a product with high purity and yield, with minimum level of impurities, preferably absent, coupled with ease of operation and, more importantly, with low production cost.

In methods disclosed in prior art, synthesis of Cefprozil has essentially been carried out by amidification of a 7-amino-3-(1-propen-1-yl)-cephem derivative with α-amino-p-hydroxyphenylacetic acid or its reactive derivative as disclosed in the following patents.

U.S. Pat. Nos. 4,520,022 and 4,699,979 (Hoshi et al.) disclose a synthetic process for preparation of Cefprozil by condensation of benzhydryl-7-amino-3-halomethyl-3-cephem-4-carboxylate with D-2-(t-butoxycarbonylamino)-2-(p-hydroxyphenyl)acetic acid in the presence of N,N'-dicyclohexylcarbodiimide (DCC) as the coupling agent and subsequent fuctionalization of the 3α position by Wittig reaction. The chemistry is summarized hereinbelow in Scheme I.

Scheme I:
Synthesis of Cefprozil as per the method disclosed in U.S. 4,520,022 and U.S. 4,699,979

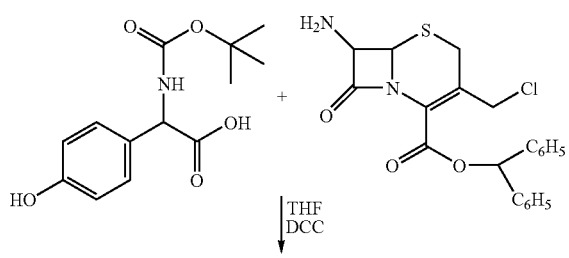

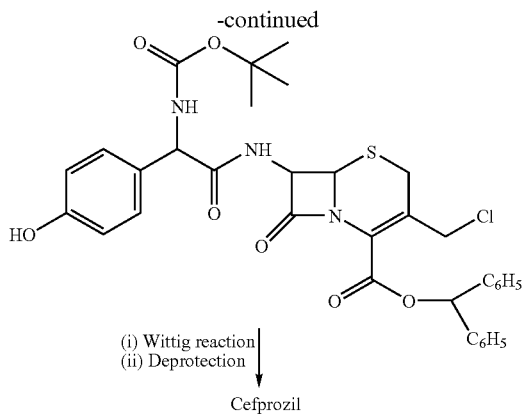

-continued (i) Wittig reaction
(ii) Deprotection

Cefprozil

One of the limitations of the process is that it employs DCC which is toxic, expensive and requires rigorous anhydrous conditions. Also dicylohexylurea is formed as a byproduct during the process, removal of which calls for several tedious chromatographic purification and isolation steps to be employed to get the product in pure form.

U.S. Pat. Nos. 3,970,651, 3,985,747 and GB 1,532,682 disclose methods for preparation of Cefprozil, Cefadroxil and Cefatrizine which generally comprise reaction of 4-hydroxyphenylglycine with phosgene, followed by addition of gaseous hydrogen chloride to give 4-hydroxyphenylglycine chloride hydrochloride. This is further reacted with a suitable 7-amino-3-substituted cephem derivative to give the desired cephalosporin antibiotic.

However, these methods employ toxic and hazardous phosgene and gaseous HCl, which are difficult to handle on an industrial scale and cause environmental problem.

PCT application WO 98/04732 discloses a method for preparation of Cefprozil comprising reaction of 4-hydroxyphenylglycine with ethylene glycol to give an ester which is reacted with 7-Amino-3-(propen-1-yl)-3-cephem-4-carboxylic acid (7-APCA), of formula (II), in presence of enzyme, acylase. However, this method utilizes excess amount of the expensive enzyme rendering the method uneconomical.

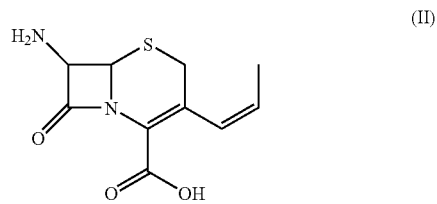

(II)

A salt of 7-APCA with amidine and its use in the production of Cefprozil is disclosed by Greil et al. in the PCT application WO03/011871. The application describes the production of Cefprozil by the reaction of an amidine salt of 7-APCA with a mixed carboxylic acid anhydride of a N-substituted-α-amino-p-hydroxyphenylacetic acid. The patent does not comment on the purity or yield of the product.

All the prior art methods discussed hereinabove are associated with the formation of varying amounts of impurities which affect the overall yield and the quality of the product. Also removal of these impurities calls for additional purification and isolation steps which render the process lengthy and tedious.

Regulatory authorities all over the world are becoming very stringent about the purity of an approved drug. Especially there is growing concern about the nature and level of impurities present in such molecules. US Pharmacopoeia specifies that the purity of Cefprozil should be between 90 to 105%. However, most of the prior art methods are associated with the formation of varying amounts of impurities and hence do not give product conforming to this criterion.

Cephalosporin antibiotics carrying the D-α-amino-α-(4-hydroxyphenyl)acetamido addendum at the 7-position such as Cefprozil and Cefadroxil are generally prepared by reacting the respective 7-amino-3-substituted-3-cephem-4-carboxylic acid or its salt/derivative with an activated derivative of 4-hydroxyphenylglycine such as a reactive ester, a reactive amide or a mixed acid anhydride. However, use of reactive amide or esters makes it difficult to obtain the desired product in high purity and yield because of the occurrence of side-reactions as well as racemization.

Of the activated derivatives of 4-hydroxyphenylglycine, the mixed anhydride of α-amino-p-hydroxyphenylacetic acid of formula III or IIIa:

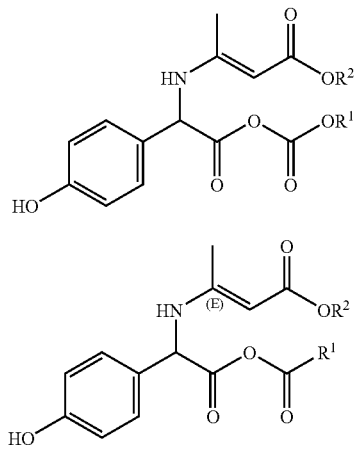

wherein R1 is an alkyl or an aryl group and R2 is methyl or ethyl, is generally prepared by reacting N-substituted-α-amino-p-hydroxyphenylacetic acid or its salt (Dane salt) with an appropriate acylating agent at an appropriate temperature. For example in the process disclosed in U.S. Pat. No. 3,985,741, the mixed anhydride is prepared by adding the acylating agent, base and the Dane salt to dry acetone at −10° C. and stirring the slurry for 20 minutes. As per the process disclosed in U.S. Pat. No. 4,218,474, the mixed anhydride is prepared by adding a chloroformate, such as ethylchloroformate, to a solution of N-protected-4-hydroxy phenylglycine dissolved in an inert organic solvent at a temperature of −5° to 0° C. in the presence of a base. According to the method disclosed in WO03/011871, the mixed acid anhydride is prepared by adding a base and Dane salt to an inert organic solvent at ambient temperature, cooling the suspension to −30° C., followed by addition of the acylating agent and stirring.

Most of the prior art methods for preparation of the mixed acid anhydride are associated with the formation of varying amounts of different impurities. For example, during the preparation of mixed the 4-hydroxy group of the Dane salt is likely to react with the acylating agent thereby forming an impurity which further reacts with 7-APCA or its salts to form an impurity of formula (IV).

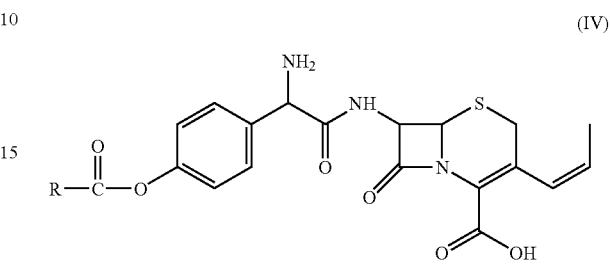

During the course of the present invention, the inventors have reproduced the process for preparation of Cefprozil as disclosed in WO03/011871. It was observed that the preparation of mixed acid anhydride by the method reported in WO03/011871 and its subsequent reaction with amidine salt of 7-APCA is associated with the formation of impurities in the range of 6-7%. Preparation of mixed anhydride as disclosed in U.S. Pat. No. 3,985,741 and its subsequent reaction with 7-aminodesacetoxycephalosporanic acid (7-ADCA) or a salt thereof gives 37% conversion to Cefadroxil of formula (V) with impurities to the tune of 30-35%.

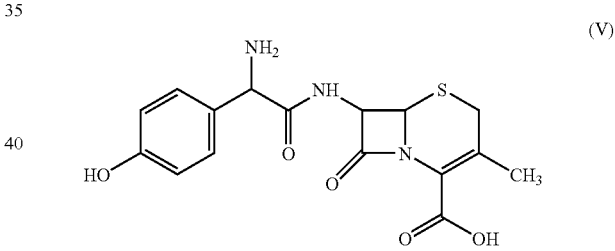

In the prior art methods, cephalosporin antibiotics such as Cefprozil and Cefadroxil have been prepared by reacting the mixed acid anhydride with respective 7-amino-3-substituted-3-cephem-4-carboxylic acid or its salt/derivative such as an amidine salt of 7-APCA as disclosed in WO03/011871 and 7-ADCA or its salt as disclosed in U.S. Pat. No. 3,985,741. However, use of 7-amino-3-substituted-3-cephem-4-carboxylic acid, its acid salt or an amidine salt as disclosed in these prior art methods is found to give the product in low yield due to side reactions of the unprotected 4-carboxylic acid group and 7-amino group.

Hence there is a need to for a protected form of 7-APCA, which will activate the amino group in the 7-position, efficiently protect the carboxylic acid group, which will not require additional deprotection steps and can be deprotected in-situ during reaction work-up.

In summary, the prior art methods for preparation of Cefprozil:

i) utilize toxic and expensive chemicals such as phosgene, DCC and HCl;

ii) utilize expensive enzyme like acylase; and iii) are associated with formation of varying amounts of impurities which give the product in low purity and yield, rendering such methods less cost effective.

Therefore, a need exists for a simple and cost-effective method for the preparation of Cefprozil in high purity and yield. Such a need could be met through minimization of the impurities associated with the prior art methods with concurrent improvement in the purity and yield of the product.

OBJECTS OF THE INVENTION

It is an object of the present invention to provide an improved method for the synthesis of Cefprozil of formula (I), which dispenses with the deficiencies of the prior art methods.

It is another object of the present invention to provide an improved method for preparation of Cefprozil in high purity and yield, substantially free of impurities.

It is yet another object of the present invention to synthesize Cefprozil in high purity, substantially free of impurities by a simple and cost-effective method which comprises preparation of mixed acid anhydride and its condensation with a protected 7-APCA.

It is also an object of the present invention to provide an improved method of preparation of mixed acid anhydride by selecting the sequence and temperature of addition of the reagents, which will result in minimization of impurities.

It is a further object of the invention to demonstrate the use of a silylated derivative of 7-APCA which further aids the minimization of impurities in the product and results in product of high purity.

In their endeavor to find a simple, efficient, cost-effective process for the manufacture of Cefprozil in high yield and purity, the present inventors have surprisingly found that the sequence of addition of reagents during mixed anhydride preparation influences the amount of impurity formed.

In the prior-art methods, wherein the sequence of addition is such that the Dane salt and the acylating agent are added first, the free acylating agent tends to react with the hydroxy group and leads to the formation of impurity of formula (IV) in higher quantities.

The present inventors have found that the mixed carboxylic acid anhydride of a N-substituted-α-amino-p-hydroxy phenylacetic acid or its salt (Dane salt) can be prepared by a careful selection of a specific sequence and temperature for addition of the reagents so that it will result in minimization of impurities during product formation.

Another surprising observation during the course of present invention was that use of protected form of 7-APCA, specially disilylated 7-APCA of formula (VI), results in reduced quantities of impurities.

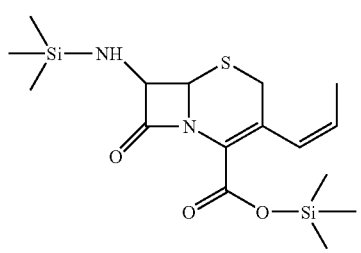

(VI)

Thus, one of the important aspects of the invention is the use of disilylated 7-APCA of formula (VI) for the synthesis of Cefprozil.

Silylation of 7-APCA has a dual role such that it protects the carboxylic acid group in the 4$^{th}$ position as well as activates the amine group in the 7$^{th}$ position. Thus, silylation eliminates the possibility of side reactions involving the carboxylic group and enhances the reactivity of the amine group by activating it.

Silylation is known to enhance the solubility of 7-amino-cephem-carboxylic acids in anhydrous solvents in which the acylation reaction is preferably conducted. Also removal of silyl group is very simple as compared to other protecting groups in the sense that it can be removed by simple hydrolysis.

SUMMARY OF THE INVENTION

In summary, the present invention provides a highly selective method for preparation of compound (I) in high yield and high purity, substantially free of impurities, which is simple, convenient and cost-effective and more importantly does not suffer from the limitations associated with the prior art methods.

Thus the main aspect of the present invention relates to process for preparation of Cefprozil of formula (I)

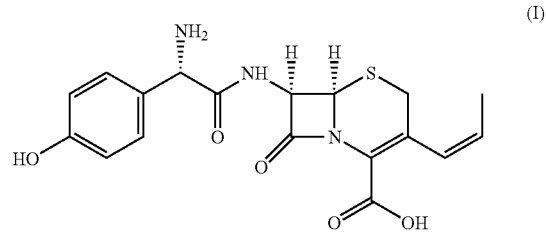

in the form of a monohydrate comprising of reacting a mixed acid anhydride of α-amino-p-hydroxy phenylacetic acid of formula (III) or (IIIa)

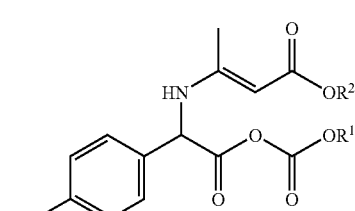

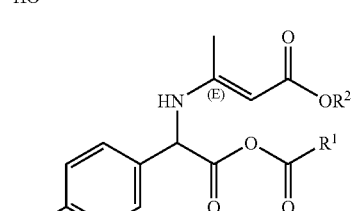

wherein R$^1$ is an alkyl or an aryl group and R$^2$ is methyl or ethyl, with a protected 7-amino-3-(propen-1-yl)-3-cephem-4-carboxylic acid of formula (VII)

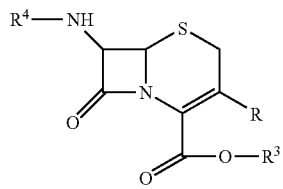

(VII)

wherein R³ and R⁴ are protective groups, R is propen-1-yl, followed by hydrolysis, isolation and purification to give Cefprozil of formula (I) in the form of a monohydrate in high yield and purity, substantially free of impurities.

DETAILED DESCRIPTION OF THE INVENTION

The inventors have found that the selection of the sequence of preparation of the mixed anhydride and the selection of the silylated derivative of 7-APCA has led to the product in high yield and with substantially less impurities.

The selection of silylated derivative of 7-APCA over the other salts as well as the selection of temperature and sequence of addition of reagents for mixed anhydride preparation is established through comparison of experimental results as stated below.

The amount of carbonate impurity of structure (IV), wherein R is ethoxy group, as well as other impurities vary with the sequence of addition and temperature of addition of the reagents during mixed anhydride preparation.

The effect of varying sequence addition of reagents during mixed anhydride preparation on the amount of total impurities formed along with Cefprozil was established by the following experimental evidence.

(i) If the sequence of addition of the reagents during mixed anhydride preparation is altered in such a way that the Dane salt is first added to a solvent or a mixture thereof at −50° C., the temperature of the suspension is raised to ambient followed by addition of acylating agent and then base, then the product Cefprozil is found to contain total impurities to the tune of 4.6%.

(ii) If the Dane salt is first added to a solvent or a mixture thereof at −50° C., the temperature of the suspension is raised to ambient followed by addition of base and then the acylating agent, then the total impurities observed, after condensation with disilylated 7-APCA, amount to 2.94%.

(iii) If the sequence of addition is such that the acylating agent and base are added to a solvent or a mixture of an inert organic solvent and a polar aprotic solvent at ambient temperature, the suspension is cooled to −35° to −50° C. followed by addition of Dane salt, and the mixed anhydride thus prepared is reacted with a silylated derivative of 7-APCA the total impurities are reduced to 2.26%.

(iv) Further, if the acylating agent and base are added to an inert organic solvent at ambient temperature, the suspension is cooled to −35° to −50° C., Dane salt is added to the cooled suspension, followed by addition of a of a polar aprotic solvent to the solution, then the total impurities formed alongwith Cefprozil are reduced to 0.64%.

The qualitative results as monitored after condensation reaction by HPLC are tabulated hereinbelow.

Effect of Sequence of Addition of Reagents in Preparation of Mixed Anhydride on the Level of Impurities

| Sequence of addition of reagents during mixed anhydride preparation. | HPLC monitoring method results | | | |
|---|---|---|---|---|
| | Unconverted starting material % | Product % | Carbonate impurity (IV) formed during reaction % | Total impurity formed during reaction, % |
| (i) | 5.10 | 90.3 | 2.31 | 4.6 |
| (ii) | 2.97 | 94.09 | 1.81 | 2.94 |
| (iii) | 4.99 | 92.74 | 0.3 | 2.26 |
| (iv) | 0.56 | 98.78 | 0.45 | 0.64 |

In the present invention, the preferred sequence of addition is such that the acylating agent and base are mixed first so that they form a complex. Dane salt is then added so that the acylating agent-base complex reacts preferentially with the carboxylic acid group and very little amount of the free acylating agent is available for reaction with the hydroxyl group and hence results in reduced quantities of impurity (IV) as well as other impurities.

Thus according to one aspect the preferred sequence of addition of reagents for the preparation mixed anhydride is:
Sequence (iii) i.e.
(a) adding an acylating agent and a base to a mixture of an inert organic solvent and a polar aprotic solvent at ambient temperature;
(b) cooling the solution to low temperature;
(c) addition of Dane salt of an α-amino-p-hydroxy phenylacetic acid to the cooled solution and agitation.

According to another aspect the preferred sequence of addition of reagents for the preparation mixed anhydride is
Sequence (iv) i.e.
(a) adding an acylating agent and a base to an inert organic solvent at ambient temperature;
(b) cooling the solution to low temperature;
(c) addition of Dane salt of α-amino-p-hydroxy phenylacetic acid to the cooled solution and agitation.
(d) addition of a polar aprotic solvent to the above solution and agitation at low temperature.

The temperature of addition of reagents during mixed anhydride preparation is equally effective in suppressing the amount of total impurities formed.

i) For example, in the present invention, if the addition of the reagents in mixed anhydride preparation is done sequentially as described in sequence (iii) or (iv), but at a uniform temperature of 20° to 25° C. followed by its reaction with a silylated derivative of 7-APCA, then the impurities formed add up to 18% and conversion to the product is reduced to 4%.

ii) If the acylating agent and base are added to a solvent or a mixture thereof at 50° C., the suspension cooled to −35° to −50° C. followed by addition of the Dane salt and agitation at −35° to −50° C. followed by its reaction with a silylated derivative of 7-APCA, then the total impurities to the tune of 7.73% are observed in the reaction mass.

iii) If the addition of the reagents in mixed anhydride preparation is done sequentially as described in sequence (iii) or (iv) at −50° C., then the impurities are reduced to 3.68%.

iv) The total impurities are reduced to 2.26% when in the mixed anhydride preparation, addition of an acylating agent and a base to a solvent or a mixture of an inert organic solvent and a polar aprotic solvent is conducted at 20° to 25° C., the suspension cooled to −35° to −50° C. followed by addition of Dane salt and agitation at −35° to −50° C. and the mixed anhydride thus prepared is reacted with a silylated derivative of 7-APCA. Also at this selection of temperature and sequence of addition of the reagents, the formation of carbonate impurity of structure (IV) wherein R is ethoxy is reduced to 0.3% as against 1-1.5% for other temperature combinations.

v) When in the mixed anhydride preparation, addition of an acylating agent and a base to an inert organic solvent is conducted at 20° to 25° C., the suspension cooled to −35° to −50° C. followed by addition of Dane salt and a polar aprotic solvent and agitation at −35° to −50° C. and the mixed anhydride thus prepared is reacted with a silylated derivative of 7-APCA, then the total impurities are reduced to 0.64%.

The qualitative results as monitored after condensation reaction by HPLC are tabulated hereinbelow.

Effect of Temperature in Preparation of Mixed Anhydride on the Level of Impurities

| Reaction temperature | | HPLC monitoring method results | | | |
|---|---|---|---|---|---|
| Step (a) temperature*, ° C. | Step (c) and/or temperature#, ° C. | Unconverted starting material % | Product % | Carbonate impurity (IV) formed during reaction % | Total impurity formed during reaction, % |
| 20–25 | 20–25 | 77.59 | 4.42 | 1.43 | 18 |
| 45–50 | −35 to −50 | 3.56 | 88.71 | 1.41 | 7.73 |
| −50 | −35 to −50 | 1.07 | 95.25 | 1.03 | 3.68 |
| 20–25 | −35 to −50 | 4.99 | 92.74 | 0.3 | 2.26 |
| 20–25 | −35 to −50$ | 0.56 | 98.78 | 0.45 | 0.64 |

*temperature of addition of acylating agent and a base to an inert organic solvent or a mixture thereof.
temperature of addition of Dane salt of α-amino-p-hydroxy phenylacetic acid and agitation of the reaction mass.
$temperature of addition of Dane salt and agitation of the reaction mass followed by addition of a polar aprotic solvent and agitation.

Thus, the selective preparation of mixed anhydride and the use of novel protected form of 7-APCA, viz. disilylated 7-APCA, in the preparation of Cefprozil, results in the reduction of impurities associated with the prior-art methods.

For example, If the mixed anhydride is prepared by the method as described in WO03/011871, which comprises of addition of 4-picoline and Dane salt to a mixture of DCM and DMF, cooling the suspension to −30° C. followed by addition of the acylating agent and agitating the suspension at −25° to −20° C. and cooling it to −50° C., followed by its reaction with an amidine salt of 7-APCA, then 6-7% impurity is observed in the reaction mass as against the 2.26% impurity observed in the method of present invention.

Comparison of the Method of Present Invention with the Method as Disclosed in WO 03/011871 and Reproduced by the Inventors

| | HPLC monitoring method results | | | |
|---|---|---|---|---|
| Process | Unconverted starting material % | Product % | Total impurity in reaction mass, % | Yield of isolated Cefprozil monohydrate, % |
| Present invention | 4.99 | 92.74 | 2.26 | 70.7 |
| WO 03/011871 | 10.23 | 76.29 | 6.4 | 62.8 |

The process of present invention results in a product of high yield and purity by way of a selective use of mixed anhydride of formula (III), obtained by following a specific sequence and temperature of operation, and the use of a novel protected form of 7-APCA, viz. disilylated 7-APCA of formula (VI). It is a combination of both these parameters that results in reduction of impurities. This is further substantiated by experimental evidence which is tabulated hereinbelow.

| | HPLC monitoring method results | | |
|---|---|---|---|
| Process | Unconverted starting material, % | Product, % | Total impurity in reaction mass, % |
| Mixed anhydride prepared as per prior-art method + silylated 7-APCA | 41.59 | 57.5 | 0.91 |
| Mixed anhydride prepared by method of present invention + 7-APCA | 89.2 | 0.28 | 10.51 |
| Present invention: Mixed anhydride prepared by method of present invention + silylated 7-APCA | 4.99 | 92.74 | 2.26 |
| Mixed anhydride prepared by method of present invention + guanidine salt of 7-APCA | 2.4 | 92.6 | 4.9 (Impurities are double that of c)) |

From the abovementioned, it is obvious that the impurities formed are lowest for the process of present invention.

The HPLC method details are as under:

Mobile Phase:
(A) Buffer and Acetonitrile (90:10).
(B) Buffer and Acetonitrile (30:70).
Both adjusted to pH 4.4 by orthophosphoric acid
Chromatographic system:

| Column: | Kromasil C-18 (4.6 × 250 mm), 5μ | | |
|---|---|---|---|
| Flow rate: | 1.0 ml/minute. | Auto sampler temperature: | 10° C. |
| Detector: | UV at 280 nm. | Injection volume: | 20 μl. |
| Run time: | 90 minutes. | Temperature: | Ambient. |

Time Program:

| Time(min) | Mobile phase (A) | Mobile phase (B) |
|---|---|---|
| 0.01 | 100 | 0 |
| 10.0 | 100 | 0 |
| 40.0 | 0 | 100 |
| 70.0 | 0 | 100 |
| 80.0 | 100 | 0 |
| 90.0 | STOP | |

Thus, one aspect of the invention relates to a simple, efficient, cost-effective method for manufacture of Cefprozil of formula (I) in high purity and yield.

Another aspect of the invention relates to a process for preparation of mixed acid anhydride of a N-substituted-α-amino-p-hydroxyphenylacetic acid, by selecting the sequence and temperature of addition of the reagents.

According to a preferred aspect of the invention, there is provided a process for preparation of Cefprozil in the form of a monohydrate, comprising steps of: reacting a mixed acid anhydride of α-amino-p-hydroxy phenylacetic acid of formula (III) or (IIIa)

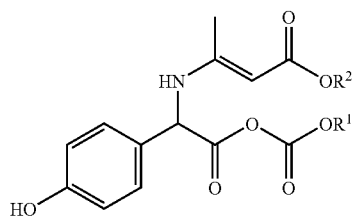

(III)

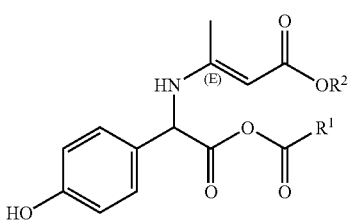

(IIIa)

wherein $R^1$ is an alkyl or an aryl group and $R^2$ is methyl or ethyl, the mixed acid anhydride prepared by a process comprising the steps of (a) adding an acylating agent and a base to a mixture of an inert organic solvent and a polar aprotic solvent at a temperature in the range of 0° to 40° C., preferably 20° to 25° C.;

(b) cooling the solution to a temperature in the range of −70° to −30° C., preferably −35° C. to −50° C.;

(c) addition of Dane salt of an α-amino-p-hydroxy phenylacetic acid to the cooled solution and agitation at a temperature in the range of −70° to −30° C., preferably −35° C. to −50° C.

with a protected 7-amino-3-(propen-1-yl)-3-cephem-4-carboxylic acid (7-APCA of formula (VII)

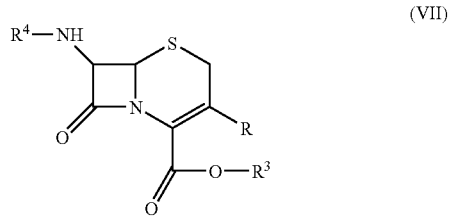

(VII)

wherein $R^3$ and $R^4$ are protective groups, R is propen-1-yl, followed by hydrolysis, isolation and purification to give Cefprozil of formula (I) in the form of a monohydrate in high yield and purity, substantially free of impurities.

According to a preferred aspect of the invention, there is provided a process for preparation of Cefprozil in the form of a monohydrate, comprising steps of:

reacting a mixed acid anhydride of α-amino-p-hydroxy phenylacetic acid of formula (III) or (IIIa)

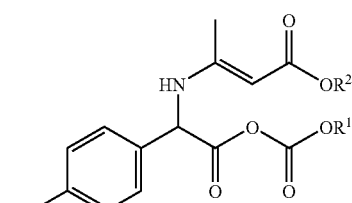

(III)

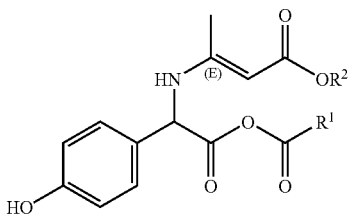

(IIIa)

wherein $R^1$ is an alkyl or an aryl group and $R^2$ is methyl or ethyl, the mixed acid anhydride prepared by a process comprising the steps of (a) adding an acylating agent and a base to an inert organic solvent at a temperature in the range of 0° to 40° C., preferably 20° to 25° C.;

(b) cooling the solution to a temperature in the range of −70° to −30° C., preferably −35° C. to −50° C.;

(c) addition of Dane salt of an α-amino-p-hydroxy phenylacetic acid to the cooled solution and agitation at a temperature in the range of −70° to −30° C., preferably −35° C. to −50° C.

(d) addition of a polar aprotic solvent to the above solution and agitation at a temperature in the range of −70° to −30° C., preferably −35° C. to −50° C.

with a protected 7-amino-3-(propen-1-yl)-3-cephem-4-carboxylic acid (7-APCA) of formula (VII)

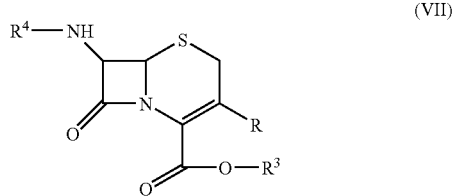

(VII)

wherein $R^3$ and $R^4$ are protective groups, R is propen-1-yl, followed by hydrolysis, isolation and purification to give Cefprozil of formula (I) in the form of a monohydrate in high yield and purity, substantially free of impurities.

Preferably the protected form of 7-APCA is the silylated form of 7-APCA. 7-APCA of formula (II) can be protected by silylation using a suitable silylating agent in an inert organic solvent or a mixture thereof over a wide temperature range, e.g. ambient to reflux temperature of the solvent system, preferably at the reflux temperature.

The mixed acid anhydride is condensed with the silylated compound at a temperature in the range of −90° to −30° C. but preferably between −50° to 40° C. and the silylated product is subsequently hydrolyzed to give Cefprozil in high purity, substantially free of impurities.

Cefprozil so obtained can be isolated preferably in the form of a solvate e.g. N,N-dimethylformamide solvate and subsequently purified to obtain Cefprozil in the form of a hydrate e.g. a monohydrate.

The method for preparation of Cefprozil monohydrate in high purity, substantially free of impurities, as per the current invention comprises of the following steps;

A. Preparation of Mixed Carboxylic Acid Anhydride

The mixed acid anhydride, employed in the present invention has been prepared by an improved process which comprises of:

(a) adding an acylating agent and a base to a mixture of an inert organic solvent and a polar aprotic solvent at a temperature in the range of 0° to 40° C., preferably 20° to 25° C.;

(b) cooling the solution to a temperature in the range of −70° to −30° C., preferably −35° C. to −50° C.;

(c) addition of Dane salt of an α-amino-p-hydroxy phenylacetic acid to the cooled solution and agitation at a temperature in the range of −70° to −30° C., preferably −35° C. to −50° C.

The mixed acid anhydride, employed in the present invention may also be prepared by an improved process which comprises of:

(a) adding an acylating agent and a base to an inert organic solvent at a temperature in the range of 0° to 40° C., preferably 20° to 25° C.;

(b) cooling the solution to a temperature in the range of −70° to −30° C., preferably −35° C. to −50° C.;

(c) addition of Dane salt of an α-amino-p-hydroxy phenylacetic acid to the cooled solution and agitation at a temperature in the range of −70° to −30° C., preferably −35° C. to −50° C.

(d) addition of a polar aprotic solvent to the above solution and agitation at a temperature in the range of −70° to −30° C., preferably −35° C. to −50° C.

In a specific embodiment of the present invention, the mixed anhydride is prepared from the N-substituted-α-amino-p-hydroxyphenyl acetic acid or its salt e.g. Dane salt such as sodium or potassium D-N-(1-methoxycarbonylpropene-2-yl)-α-amino-p-hydroxyphenyl acetate or sodium or potassium D-N-(1-ethoxycarbonylpropene-2-yl)-α-amino-p-hydroxyphenyl acetate. The Dane salt is activated with acylating agents such as reactive forms of aliphatic, alicyclic or aromatic acids e.g. acid halogenides such as pivaloyl chloride and benzoyl chloride, and esters such including chloroformic acid alkyl esters, such as ethyl chloroformate. The activation is carried out in an inert organic solvent or a mixture of an inert organic solvent and a polar aprotic solvent, at a temperature in the range of 0° to 40° C., preferably 20° to 25° C. followed by addition of a base and acylating agent to the solvent mixture at that temperature. The acylating agent is used in molar to slight excess with respect to the Dane salt, preferably 1-1.5 moles of acylating agent per mole of Dane salt are employed. The base is used in the range of 0.02-0.04 moles with respect to the Dane salt. The resulting mass is cooled to −70° to −40° C., preferably −35° to 50° C. and the Dane salt is then added and the reaction is continued at this temperature for 60-180 minutes, preferably 90-120 minutes. A polar aprotic solvent is now added (if not added at the beginning) and the reaction mass is agitated for 10-60 minutes, preferably 20-40 minutes. The final reaction mass containing the mixed anhydride is cooled to −75° to −60° C. and maintained at this temperature for further reaction.

Examples of suitable acylating agents for the above process include reactive forms of aliphatic, alicyclic, or aromatic acids such as chloroformic acid, benzoic acid, pivalic acid and 2-ethylhexanoic acid. The reactive forms of these acids include their esters such as ethyl chloroformate, isobutyl chloroformate and their halogenides like pivaloyl chloride, 2-ethyl-hexanoyl chloride and benzoyl chloride. The preferred acylating agent is ethyl chloroformate.

In step A, a suitable base is employed as a catalyst selected from triethylamine, picoline, N-methylmorpholine, N,N-dimethylbenzylamine, lutidine, N,N-dimethyl-4-aminopyridine, N,N-dicyclohexylamine. The preferred base is N-methylmorpholine.

Suitable inert organic solvents employed for the reaction include, but are not limited to methylene chloride, tetrahydrofuran, chloroform, diethyl ether, chlorotethane, acetonitrile, trichloroethylene, and ethyl acetate. Methylene chloride is the preferred inert organic solvent.

Suitable polar aprotic solvents employed for the reaction include, but are not limited to N,N-dimethyl formamide, acetone, acetonitrile, dimethyl sulphoxide and dimethyl acetamide. N,N-dimethyl formamide is the preferred polar aprotic solvent.

B. Silylation of the 3-substituted-7-aminocephalosporanic acids

Use of silylated 7-APCA also forms another novel aspect of the present invention which further aids the minimization of impurities in the product and results in product of high purity.

Silylation of 7-APCA is preferably conducted in a suitable inert organic solvent or a mixture of an inert organic solvent and a polar aprotic solvent, such as those used for the mixed anhydride preparation, by using known silylating agents over a wide temperature range, e.g. ambient to reflux temperature of the solvent system, preferably at the reflux temperature. The silylating agent may be used in molar equivalent or excess with respect to 7-APCA, preferably in a molar ratio of 1-2 with respect to 7-APCA. The reaction time is between 2-5 hours, preferably 4 hours. The silylated mass is cooled to −70° to −50° C. prior to condensation with the mixed acid anhydride.

Silylating agents useful in the above process are known in the art [see, for example, U.S. Pat. Nos. 3,654,266, 3,575,970, 3,499,909, 3,595,855, 3,249,622 and U.K. Pat. Nos. 1,339,605, 959,853 and 1,008,468]. Any appropriate silylating agent known in the art could be employed. Examples of suitable silylating agents include hexamethyldisilazane, hexaethyldisilazane, trimethylchlorosilane, triethylchlorosilane, methyltrichlorosilane, methyldiethylchlorosilane, dimethylethylchlorosilane, triethylbromosilane, tri-n-propylchlorosilane, bromomethyldimethylchlorosilane, tri-n-butylchlorosilane, triphenylfluorosilane, hexa-p-tolyldisilazane, triphenylsilylamine, phenylethylmethylchlorosilane, phenyldimethylbromosilane, hexaphenyldisilazane, N-ethyltriethylsilylamine, tetraethyldimethyldisilazane, N,O-bis-trimethylsilyl acetamide, tetramethyldiethyldisilazane, or mixtures thereof. The most preferred silylating agents are N,O-bis-trimethylsilyl acetamide, trimethylchlorosilane and hexamethyldisilazane or a mixture thereof.

C. Condensation

The silylated mass prepared as in step B is added to the mixed anhydride mass prepared as in step A at a temperature in the range of −90° to −30° C. but preferably between −70° to −60° C. After the addition is completed, the reaction mass is agitated at −60° to −30° C., preferably −50° to −40° C. till quantitative conversion to the silylated Cefprozil is achieved. The reaction time required for the reaction to go to completion could be between 2 to 5 hours, preferably 4 hours.

D. Isolation and Purification

The cephalosporanic acid obtained in the protected form may be deprotected by appropriate methods e.g. by adding dilute mineral acid such as hydrochloric acid, sulphuric acid, nitric acid, but preferably dilute hydrochloric acid. The aqueous layer may then be diluted with a solvent and optionally the solid impurities may be removed at this stage of the process by treatment with activated carbon and/or filter aid.

The product obtained is isolated and purified by conventional methods. Particularly, the desired Cefprozil monohydrate may be obtained in its pure and crystalline form through its solvate preferably in the form of an N,N-dimethylformamide solvate. The DMF solvate is prepared by the process as disclosed in U.S. Pat. No. 4,694,079, which comprises of adding chilled N,N-dimethylformamide to the aqueous layer over a period of 30 minutes while maintaining the temperature between 10° to 15° C. The pH of the filtrate is adjusted to 4-7, by slow addition of an inorganic base selected from aqueous ammonia, sodium bicarbonate, sodium hydroxide but preferably aqueous ammonia solution. The solution may then be optionally seeded with the solvate crystals. The solution is agitated at 25° to 30° C. to achieve complete crystallization of the DMF solvate. The resulting solid is filtered and washed with solvent preferably DMF and/or ethyl acetate to obtain the DMF solvate of Cefprozil.

Desolvation may be carried out by dissolving the DMF solvate of Cefprozil in water or a mixture of water and an organic solvent such as acetonitrile, ethyl acetate, acetone or a $C_1$ to $C_5$ alkanol at a temperature of 0° to 20° C. The solution may be optionally seeded with the crystalline product and the slurry is agitated for 30-90 minutes. The solid product so obtained is filtered and may be washed with water and/or a solvent. The solid product is finally dried under vacuum at 30° to 45° C. to obtain high purity Cefprozil of formula (I) in the form of a hydrate e.g. a monohydrate in high purity, conforming to pharmacopoeial specifications.

The improved process resulted in a significant improvement in the yield and quality of the product. The total impurities could be reduced from 6-7%, in the reaction mixture, associated with the prior art method to 2.26% and from 0.8%, in the final isolated product to 0.48%. The process results in a significant improvement in the yield of Cefprozil monohydrate from 62.8% in the prior art method to 70.7% in the improved process.

The above process could be extended to the synthesis of Cefadroxil in high purity and yield by condensation of the mixed anhydride of α-amino-p-hydroxy phenylacetic acid with disilylated 7-aminodesacetoxycephalosporanic acid (7-ADCA).

The following examples are given by way of illustration of the present invention.

EXAMPLE-1

Step A

To a mixture of methylene chloride (125 ml) and N,N-dimethylformamide (85 ml), cooled to 20° C.-25° C., is added a solution of N-methylmorpholine in dichloromethane (0.25 g, 0.0025 mole in 5 ml) and ethyl chloroformate in dichloromethane (12.72 g, 0.117 mole in 10 ml) under stirring. The resulting solution is cooled to −40° C. to −50° C. and potassium D-N-(2-methoxycarbonyl-1-methylvinyl)-α-amino-α-(4-hydroxylphenyl)acetate (33.14 g, 0.11 mol) is added to it. The suspension is agitated at −40° C. to −35° C. for 120 minutes. The reaction mass which is a solution of mixed anhydride product is cooled to −70° C. for condensation.

Step B

7-APCA (25 g, 0.104 mole) was added to methylene chloride (100 ml) at 25° to 30° C. followed by addition of N,O-bis-trimethylsilyl acetamide (0.125 g, 0.0006 mole), trimethylchlorosilane (9.3 g, 0.086 mole) and hexamethyldisilazane (13.4 g, 0.083 mole). The reaction mass was heated to reflux temperature and refluxed for 4 hours to obtain silyated 7-amino-3-(propan-1-yl)-3-cephem-4-carboxylic acid (7-APCA)compound.

Step C

To a solution of the mixed anhydride product of procedure 1A, cooled to −70° C., is added with stirring, a cooled solution of the disilylated 7-APCA as prepared by procedure 1a. The reaction mixture is stirred at −50° to 40° C. and monitored by HPLC till quantitative conversion to the silylated Cefprozil is achieved. The reaction time is about 4 hours. The resulting reaction mass is added to a mixture of 85 ml water and 20 ml concentrated hydrochloric acid maintained at −40° C. to −20° C. The temperature of the reaction mass is raised to 5° C. to 10° C. and the pH of the solution is adjusted to 0.5 with concentrated hydrochloric acid. The reaction mass is stirred for 30 minutes and the layers are separated. The aqueous layer is diluted with acetone (75 ml) followed by the addition of 2.5 g of activated carbon and sodium dithionite (0.25 g) to remove the colored solid impurities. The reaction temperature is maintained at 10° to 15° C.

The aqueous solution containing Cefprozil as obtained above is converted to its DMF solvate as per the method disclosed in U.S. Pat. No. 4,694,079. The wet DMF solvate without drying is desolvated by stirring with a mixture of demineralised water (75 ml) and ethyl acetate (45 ml) for 60 minutes. The product is filtered and dried to give Cefprozil monohydrate in the form of an off white to pale yellow crystalline powder.

Yield: 30 gms, % Yield: 70.7, Purity: 101.2%, Total impurities: 0.45%

EXAMPLE-2

Step A

Methylene chloride (125 ml) is cooled to 20° C.-25° C., and a solution of N-methylmorpholine in dichloromethane (0.25 g, 0.0025 mole in 5 ml) and ethyl chloroformate in dichloromethane (12.72 g, 0.117 mole in 10 ml) under stirring. The resulting solution is cooled to −40° C. to −50° C. and potassium D-N-(2-methoxycarbonyl-1-methylvinyl)-α-amino-α-(4-hydroxylphenyl) acetate (33.14 g, 0.11 mol) is added to it. The suspension is agitated at −40° C. to −35° C. for 120 minutes. The reaction mass which is a solution of mixed anhydride product is cooled to −70° C. for condensation.

Step B

7-APCA (25 g, 0.104 mole) was added to methylene chloride (100 ml) at 25° to 30° C. followed by addition of N,O-bis-trimethylsilyl acetamide (0.125 g, 0.0006 mole), trimethylchlorosilane (9.3 g, 0.086 mole) and hexamethyldisilazane (13.4 g, 0.083 mole). The reaction mass was heated to reflux temperature and refluxed for 4 hours to obtain silyated 7-amino-3-(propan-1-yl)-3-cephem-4-carboxylic acid (7-APCA)compound.

Step C

To a solution of the mixed anhydride product of procedure 2A, cooled to −70° C., is added with stirring, a cooled solution of the disilylated 7-APCA as prepared by procedure 1a. The reaction mixture is stirred at −50° to −40° C. and monitored by HPLC till quantitative conversion to the silylated Cefprozil is achieved. The reaction time is about 4 hours. The resulting reaction mass is added to a mixture of 85 ml water and 20 ml concentrated hydrochloric acid maintained at −40° C. to −20° C. The temperature of the reaction mass is raised to 5° C. to 10° C. and the pH of the solution is adjusted to 0.5 with concentrated hydrochloric acid. The reaction mass is stirred for 30 minutes and the layers are separated. The aqueous layer is diluted with acetone (75 ml) followed by the addition of 2.5 g of activated carbon and sodium dithionite (0.25 g) to remove the colored solid impurities. The reaction temperature is maintained at 10° to 15° C.

The aqueous solution containing Cefprozil as obtained above is converted to its DMF solvate as per the method disclosed in U.S. Pat. No. 4,694,079. The wet DMF solvate without drying is desolvated by stirring with a mixture of demineralised water (75 ml) and ethyl acetate (45 ml) for 60 minutes. The product is filtered and dried to give Cefprozil monohydrate in the form of an off white to pale yellow crystalline powder.

Yield: 33.4 gms, % Yield: 78.7, Purity: 101.3%, Total impurities: 0.5%

We claim:

1. A process for preparation of Cefprozil of formula (I)

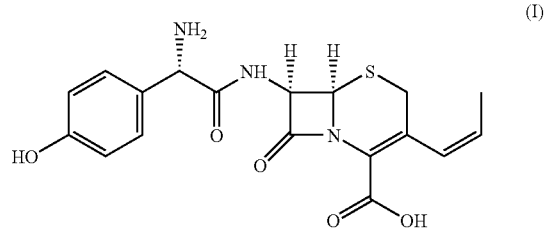

in the form of a monohydrate, the process comprising:
condensing a mixed acid anhydride of α-amino-p-hydroxy phenylacetic acid of formula (III)
wherein $R^1$ is an alkyl or an aryl group, and $R^2$ is methyl or ethyl,
with a protected 7-amino-3-(propen-1-yl)-3-cephem-4-carboxylic acid of formula (VII)

(III)

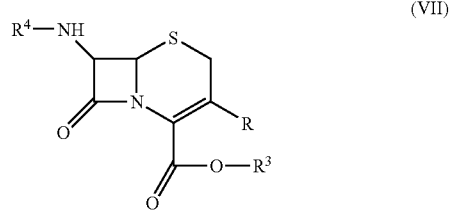

wherein $R^3$ and $R^4$ are protective groups, and R is propen-1-yl, followed by hydrolysis, isolation and purification to give Cefprozil of formula (I) in the form of a monohydrate,
wherein the mixed anhydride of formula (III) is prepared by a process comprising the steps of
(a) adding ethyl chloroformate and a base to a mixture of an inert organic solvent and a polar aprotic solvent at a temperature in the range of 0° to 40° C.;
(b) cooling the solution to a temperature in the range of −70° to −30° C.;
(c) addition of Dane salt of an α-amino-p-hydroxy phenyl acetic acid to the cooled solution and agitation at a temperature in the range of −70° to −30° C.

2. A process for preparation of Cefprozil of formula (I)

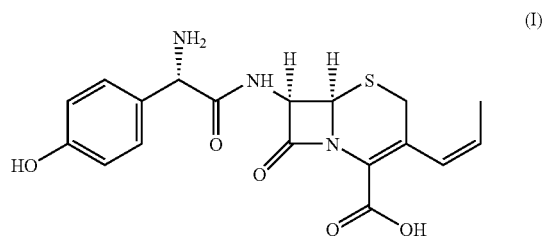

in the form of a monohydrate, the process comprising:
condensing a mixed acid anhydride of α-amino-p-hydroxy phenyl acetic acid of formula (III)

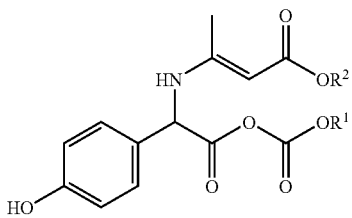

(III)

wherein R¹ is an alkyl or an aryl group and R² is methyl or ethyl, with a protected 7-amino-3-(propen-1-yl)-3-cephem-4-carboxylic acid of formula (VII)

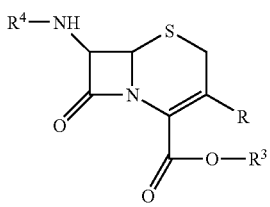

(VII)

wherein R³ and R⁴ are protective groups, R is propen-1-yl, followed by hydrolysis, isolation and purification to give Cefprozil of formula (I) in the form of a monohydrate, wherein the mixed anhydride of formula (III) is prepared by a process comprising the steps of (a) adding ethyl chloroformate and a base to an inert organic solvent at a temperature in the range of 0° to 40° C.;

(b) cooling the solution to a temperature in the range of −70° to −30° C.;

(c) addition of Dane salt of an α-amino-p-hydroxy phenylacetic acid to the cooled solution and agitation at a temperature in the range of −70° to −30° C.;

(d) addition of a polar aprotic solvent to the above solution and agitation at a temperature in the range of −70° to −30° C.

3. A process according to claim 2, wherein the mixed acid anhydride is condensed with protected 7-amino-3-(propen-1-yl)-3-cephem-4-carboxylic acid at a temperature in the range of −90° to −30° C.

4. A process as in claim 1 wherein the protected 7-amino-3-(propen-1-yl)-3-cephem-4-carboxylic [7-APCA] of formula (VII) used

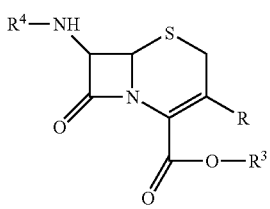

(VII)

is such that R³ and R⁴ are each a tri alkylsilyl group,

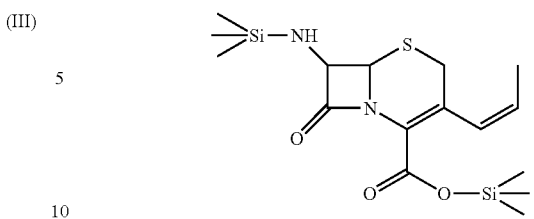

and R is propen-1-yl.

5. A process according to claim 1, wherein the inert organic solvent employed in step (a) is selected from the group consisting of methylene chloride, tetrahydrofuran, chloroform, diethyl ether, chloroethane, acetonitrile, trichloroethylene, and ethyl acetate.

6. A process according to claim 2, wherein the inert organic solvent employed in step (a) is selected from the group consisting of methylene chloride, tetrahydrofuran, chloroform, diethyl ether, chloroethane, acetonitrile, trichioroethylene, and ethyl acetate.

7. A process according to claim 1, wherein the polar aprotic solvent employed in step (a) is selected from the group consisting of N,N-dimethyl formamide, acetone, acetonitrile, dimethyl sulphoxide, and dimethyl acetamide.

8. A process according to claim 2, wherein the polar aprotic solvent employed in step (a) is selected from the group consisting of N,N-dimethyl formamide, acetone, acetonitrile, dimethyl sulphoxide, and dimethyl acetamide.

9. A process according to claim 8, wherein the polar aprotic solvent is N,N-dimethyl formamide.

10. A process according to claim 2 wherein the temperature in step (d) is in the range of −35° C. to −50° C.

11. A process according to claim 1, wherein the base employed in step (a) is selected from the group consisting of triethylamine, picoline, N-methylmorpholine, N, N-dimethylbenzylamine, lutidine, N,N-dimethyl-4-aminopyridine, and N,N-dicyclohexylamine.

12. A process according to claim 2, wherein the base employed in step (a) is selected from the group consisting of triethylamine, picoline, N-methylmorpholine, N, N-dimethylbenzylamine, lutidine, N,N-dimethyl-4-aminopyridine, and N,N-dicyclohexylamine.

13. A process according to claim 1, wherein the acylating agent employed in step (a) is in the molar ratio of 1.0 to 1.5 moles per mole of Dane salt.

14. A process according to claim 2, wherein the acylating agent employed in step (a) is in the molar ratio of 1.0 to 1.5 moles per mole of Dane salt.

15. A process according to claim 1, wherein the base employed in step (a) is in the molar ratio of 0.02 to 0.04 moles per mole of the Dane salt.

16. A process according to claim 2, wherein the base employed in step (a) is in the molar ratio of 0.02 to 0.04 moles per mole of the Dane salt.

17. A process according to claim 1 wherein the temperature in step (a) is in the range of 20° to 25° C.

18. A process according to claim 2 wherein the temperature in step (a) is in the range of 20° to 25° C.

19. A process according to claim 1, wherein the Dane salt is sodium or potassium D-N-(1-methoxycarbonylpropene-2-yl)-α-amino-p-hydroxyphenyl acetate or sodium or potassium D-N-(1-ethoxycarbonylpropene-2-yl)-α-amino-p-hydroxyphenyl acetate.

20. A process according to claim 2 wherein the Dane salt is sodium or potassium D-N-(1-methoxycarbonylpropene-2-yl)-α-amino-p-hydroxyphenyl acetate or sodium or potassium D-N-(1-ethoxycarbonylpropene-2-yl)-α-amino-p-hydroxyphenyl acetate.

21. A process according to claim 1 wherein the temperature in step (b) is in the range of −35° C. to −50° C.

22. A process according to claim 2 wherein the temperature in step (b) is in the range of −35° C. to −50° C.

23. A process according to claim 1 wherein the temperature in step (c) is in the range of −35° C. to −50° C.

24. A process according to claim 2 wherein the temperature in step (c) is in the range of −35° C. to −50° C.

25. A process according to claim 1 wherein the mixed acid anhydride is condensed with protected 7-amino-3-(propen-1-yl)-3-cephem-4-carboxylic acid at a temperature in the range of −90° to −30° C.

26. A process according to claim 25 wherein the mixed acid anhydride is condensed with protected 7-amino-3-(propen-1-yl)-3-cephem-4-carboxylic acid at a temperature in the range of −50° to −40° C.

27. A process according to claim 3 wherein the mixed acid anhydride is condensed with protected 7-amino-3-(propen-1-yl)-3-cephem-4-carboxylic acid at a temperature in the range of −50° to −40° C.

28. A silylated 7-amino-3-(propen-1-yl)-3-cephem-4-carboxylic acid according to claim 4, is of formula (VI).

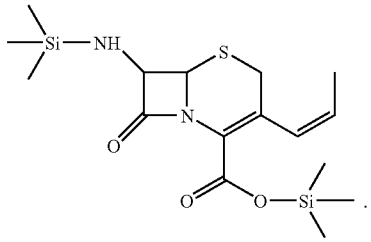

(VI)

29. A process according to claim 11, wherein the base is N-methylmorpholine.

30. A process according cc claim 12, wherein the base is N-methylmorpholine.

31. A process according to claim 2 wherein the protected 7-amino-3-(propen-1-yl)-3-cephem-4-carboxylic [7-APCA] of formula (VII) used

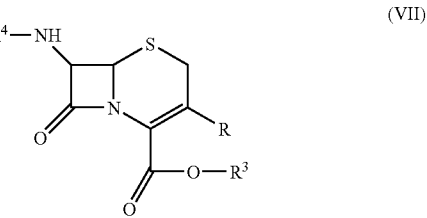

(VII)

is such that $R^3$ and $R^4$ are each tri alkylsilyl group, and R is propen-1-yl.

32. A process according to claim 7, wherein the polar aprotic solvent is N,N-dimethyl formamide.

33. A silylated 7-amino-3-(propen-1-yl)-3-cephem-4-carboxylic acid according to claim 31, is of formula (VI)

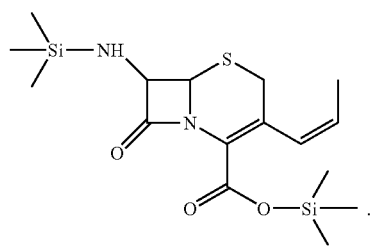

(VI)

* * * * *